United States Patent [19]

Pawlowski et al.

[11] Patent Number: 5,298,364
[45] Date of Patent: Mar. 29, 1994

[54] RADIATION-SENSITIVE SULFONIC ACID ESTERS AND THEIR USE

[75] Inventors: Georg Pawlowski, Wiesbaden; Horst Roeschert, Ober-Hilbersheim; Walter Spiess, Dieburg; Klaus-Juergen Przybilla, Frankfurt am Main, all of Fed. Rep. of Germany

[73] Assignee: Hoechst Aktiengesellschaft, Frankfurt am Main, Fed. Rep. of Germany

[21] Appl. No.: 895,679

[22] Filed: Jun. 9, 1992

[30] Foreign Application Priority Data

Jun. 19, 1991 [DE] Fed. Rep. of Germany ....... 4120174

[51] Int. Cl.$^5$ .................... G03C 1/71; G03C 1/76
[52] U.S. Cl. .................... 430/280; 430/270; 430/910; 430/919; 430/922; 522/50; 522/52; 544/180
[58] Field of Search ............. 430/270, 280, 905, 910, 430/919, 922; 544/180; 522/50, 52

[56] References Cited

U.S. PATENT DOCUMENTS

| | | | |
|---|---|---|---|
| 3,692,560 | 9/1972 | Rosenkranz et al. | 117/93.31 |
| 4,619,998 | 10/1986 | Buhr | 544/193.1 |
| 4,696,888 | 9/1987 | Buhr | 430/270 |
| 4,820,607 | 4/1989 | Aoai | 430/190 |
| 4,840,867 | 6/1989 | Elsaesser et al. | 430/156 |

FOREIGN PATENT DOCUMENTS

| | | |
|---|---|---|
| 164248 | 12/1985 | European Pat. Off. |
| 3628046 | 2/1987 | European Pat. Off. |
| 232972 | 8/1987 | European Pat. Off. |

OTHER PUBLICATIONS

F. M. Houlihan, et al., "An Evaluation of Nitrobenzyl Ester Chemistry for Chemical Amplification Resists", SPIE vol. 920, 1988, pp. 67–73.

J. V. Crivello, "Possibilities for Photoimaging Using Onium Salts", Polymer Engineering and Science, vol. 23, No. 17, Dec. 1983, pp. 953–956.

C. G. Wilson, "Organic Resist Materials–Theory and Chemistry", Introduction to Microlithography ACS Symp. Ser. 219 1983, pp. 88–159.

*Primary Examiner*—Jack P. Brammer
*Attorney, Agent, or Firm*—Foley & Lardner

[57] ABSTRACT

Sulfonic acid esters of 2,4-bistrichloromethyl-6-(mono- or dihydroxyphenyl)-1,3,5-triazine are disclosed. Also disclosed is a negative-working radiation-sensitive mixture containing such a compound in combination with a compound containing at least two acid-crosslinkable groups, and a water-insoluble polymeric binder which is soluble or at least swellable in aqueous alkaline solutions. The esters are esters of a sulfonic acid or sulfonic acids of the formula R—SO$_3$H or R'(—SO$_3$H)$_2$ with 2,4-bistrichloromethyl-6-(mono- or dihydroxyphenyl)-1,3,5-triazine of the formulae I and/or II

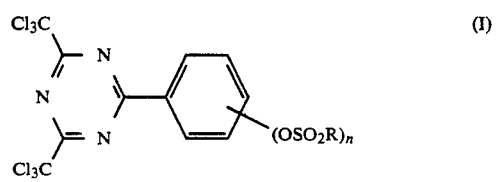

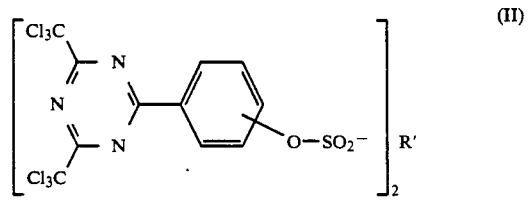

where R is an optionally further substituted (C$_1$–C$_{10}$)-alkyl, (C$_5$–C$_{10}$)cycloalkyl, (C$_6$–C$_{10}$)aryl, (C$_6$–C$_{10}$)aryl-(C$_1$–C$_{10}$)alkyl or (C$_3$–C$_9$)heteroaryl radical, R' is an optionally substituted (C$_1$–C$_{10}$)alkylene, (C$_6$–C$_{10}$)arylene or (C$_3$–C$_9$)heteroarylene radical, and n may be 1 or 2. The radiation-sensitive mixture according to the invention is remarkable for a high resolution and a high sensitivity over a wide spectral range and can be used to produce a radiation-sensitive recording material suitable for producing photoresists, electronic components, or printing plates, or for chemical milling.

15 Claims, No Drawings

RADIATION-SENSITIVE SULFONIC ACID ESTERS AND THEIR USE

BACKGROUND OF THE INVENTION

The present invention relates to sulfonic acid esters of 2,4-bistrichloromethyl-6-(mono- or dihydroxyphenyl)-1,3,5-triazine and to a negative-working radiation-sensitive mixture containing these compounds in combination with a compound containing at least two acid-crosslinkable groups, and a water-insoluble polymeric binder which is soluble or at least swellable in aqueous-alkaline solutions. The invention also relates to a radiation-sensitive recording material produced therewith which is suitable for producing photoresists, electronic components, or printing plates, or for chemical milling.

The constant reduction in the size of structures, for example, in chip production, down to the range of less than 1 μm requires modified lithographic techniques. In order to image fine structures, radiation is used which has a short wavelength, such as high-energy UV light, electron beams or X-rays. The radiation-sensitive mixture must be suited to the shortwave radiation. A summary of the requirements imposed on the radiation-sensitive mixture is provided in the paper by C. G. Willson entitled "Organic Resist Materials—Theory and Chemistry" [*Introduction to Microlithography, Theory, Materials and Processing*, edited by L. F. Thompson, C. G. Willson and M. J. Bowden, *ACS Symp. Ser.*, 219: 87 (1983), American Chemical Society, Washington]. There is therefore an increased requirement for radiation-sensitive mixtures that can be used in the more recent technologies such as mid- and deep-UV lithography [exposure, for example, to excimer lasers at wavelengths of 305 nm (XeF), 248 nm (KrF), 193 nm (ArF)], electron beam lithography or X-ray lithography. Preferably these mixtures are also sensitive in a wide spectral range and can be used in conventional UV lithography.

Negative-working radiation-sensitive mixtures that contain bisazides as crosslinking agents and binders derived from isoprene are known. They are used as radiation-sensitive layers in the production of printing plates, printed circuits and integrated circuits. Their use in microlithography is, however, limited by various technical disadvantages. Thus, it is difficult to produce high-quality layers without defects (pinholes). The thermal stability of such mixtures is inadequate, i.e., the resist images are distorted during processing by thermal flow. Finally, their resolving power is limited to structures greater than 2 μm since they exhibit undesirably high swelling even in the cured regions during the necessary development with organic solvents. This results in turn in structure distortions or inhomogeneous development processes and, consequently, in inexact reproduction of the image provided by the exposure mask.

In order to produce resist images having a resolution of better than 2 μm, other negative-working radiation-sensitive mixtures have been developed which are sensitive to radiation of shorter wavelength, for example, a mixture containing a copolymer of 2,3-epoxypropyl methacrylate and 2,3-dichloropropyl methacrylate (DCOPA) or a combination of the corresponding homopolymers. However, the glass transition temperature of this mixture is too low for many applications. In particular, the mixture has an undesirably low plasma etching resistance. In addition, this resist material has to be processed with developers containing organic solvents having low environmental acceptability. Other hitherto known negative-working photoresists with an aliphatic base also exhibit a low plasma etching resistance.

EP 164 248 discloses an acid-curable mixture that can be developed in aqueous alkali, has an improved plasma etching resistance as a result of the use of aromatics and is sensitive to near-UV light (350 to 450 nm). The acid formers mentioned in this connection are, in particular, sulfonic acid ester derivatives of diazonaphthoquinone, which form weakly acidic carboxylic acids on exposure and are therefore effective only at comparatively high concentration. However, as a result of the weak absorptions and of the inadequate bleaching-out behavior of the photolytic acid former, such mixtures have a low sensitivity to deep UV radiation, electron radiation and X-rays.

U.S. Pat. No. 3,692,560 describes an acid-curable mixture containing an acid-crosslinkable melamine derivative, a novolak and chlorinated benzophenones as photolytic acid formers. These mixtures also have inadequate sensitivity in the deep-UV region. The same applies to the acid-forming derivatives of DDT which are mentioned in EP 232 972. In addition, these are highly toxic and cannot therefore realistically be used. All the same, such compounds have an appreciable sensitivity in the deep-UV region (200 to 300 nm).

Examples of compounds that form a strong acid on irradiation include, in particular, onium salts such as diazonium, phosphonium, sulfonium and iodonium salts of non-nucleophilic acids such as $HSbF_6$, $HAsF_6$ or $HPF_6$ [J. V. Crivello, *Polym. Eng. Sci.*, 23:953 (1983)]. In addition, halogen compounds, in particular trichloromethyltriazine derivatives (EP 137 452=U.S. Pat. No. 4,619,998/4,696,888) or trichloromethyloxadiazole derivatives, o-(quinone diazide)sulfonyl chlorides, o-(quinone diazide)-4-sulfonic acid esters, bis(sulfonyl)diazomethanes, sulfonylcarbonyldiazomethanes and nitrobenzyltosylates have been recommended.

These compounds are used in negative- or positive-working radiation-sensitive mixtures. The use of such photolytic acid formers, however, entails certain disadvantages which severely restrict their possible uses in various fields of application. Thus, the onium salts have a relatively high, virtually unbleachable self-absorption in the desired wavelength region. This means that the maximum achievable resolution of the resultant radiation-sensitive mixture is limited in many cases. Furthermore, many onium salts are toxic. Their solubility in many solvents is inadequate, and for this reason only a few solvents are suitable for producing a coating solution. In addition, impurity atoms, some of which are undesirable and which may result in process interferences, particularly in microlithography, are introduced if onium salts are used, with the result that the use of such mixtures leads to unsatisfactory results. Although halogen compounds such as (quinone diazide)sulfonyl chlorides form strong hydrohalic acids, they have, in the radiation-sensitive mixture and also on certain substrates, only a limited durability. This has been improved by inserting an interlayer between substrate and radiation-sensitive layer containing compounds that form a strong acid upon exposure, but this resulted in an undesirable increase in defects and in a reduced reproducibility (DE 36 21 376=U.S. Pat. No. 4,840,867).

Although other classes of compounds that generate hydrohalic acid such as bistrichloromethyltriazine derivatives (EP 137 452) have a good acid-forming efficiency, they have an often inadequate solubility in common resist solvents. They are, in addition, frequently sweated out of the photosensitive layer under the processing conditions applied in practice, with the result that a reproducible production of the resultant layer is no longer possible.

In more recent publications by F. M. Houlihan et al., SPIE 920:67 (1988), it was shown that positive-working systems containing nitrobenzyl tosylates that form sulfonic acids with low migration tendency on exposure can be used in certain acid-labile resist formulations in addition to the above-mentioned acid formers. From these results it can be deduced that such compounds can also be used for photocurable systems. The sensitivities achieved under these circumstances and the thermal stability of the photoresist prove, however, to be inadequate.

Despite the intensive research activity hitherto carried out in this field, no radiation-sensitive mixture is known at the present time with which a negative-working radiation-sensitive recording material can be produced having a high sensitivity in the deep-UV region (200 to 300 nm), a high resolution, and an ability to be developed fully compatibly and in aqueous alkali solutions using standard lithographic processing steps.

SUMMARY OF THE INVENTION

It is therefore an object of the present invention to provide novel compounds that form strong acid on exposure to actinic radiation and a radiation-sensitive mixture containing these compounds in combination with acid-crosslinkable compounds.

It is a further object of the invention to provide a compound that photolytically forms an acid that does not have the numerous disadvantages described in greater detail above.

These and other objects according to the invention are provided by a radiation-sensitive ester of a sulfonic acid of the formula $R-SO_3H$ or $R'(-SO_3H)_2$ with 2,4-bistrichloromethyl-6-(mono- or dihydroxyphenyl)-1,3,5-triazines, said ester being represented by one of formulae I and II

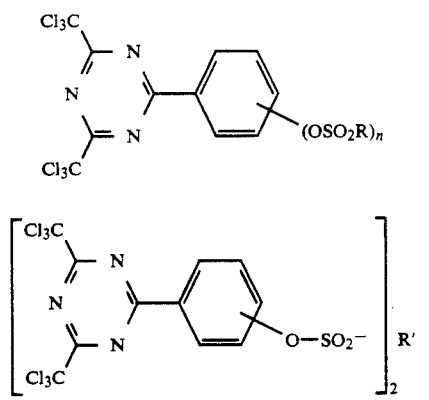

where R is an optionally further substituted $(C_1-C_{10})$-alkyl, $(C_5-C_{10})$ cycloalkyl, $(C_6-C_{10})$ aryl, $(C_6-C_{10})$ aryl-$(C_1-C_{10})$alkyl or $(C_3-C_9)$heteroaryl radical, R' is an optionally substituted $(C_1-C_{10})$alkylene, $(C_6-C_{10})$arylene or $(C_3-C_9)$heteroarylene radical, and n may be 1 or 2.

Compounds according to the invention produce a strong acid on irradiation. Also provided according to the invention is a negative-working radiation-sensitive mixture comprising (a) a compound which forms strong acid on exposure to actinic radiation, (b) a compound containing at least two acid-crosslinkable groups, and (c) a water-insoluble polymeric binder which is soluble or at least swellable in aqueous alkaline solutions, in an amount sufficient to produce a uniform film when a layer of the mixture is coated on a base, wherein the compound (a) is a sulfonic acid ester as described herein and wherein compounds (a) and (b) are present in amounts sufficient to produce insoluble, crosslinked regions when a layer of the mixture is exposed to actinic radiation.

A negative-working radiation-sensitive recording material according to the invention comprises a layer of this radiation-sensitive mixture on a base.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Compounds according to the present invention are radiation-sensitive esters of sulfonic acids of the formula $R-SO_3H$ or $R'(-SO_3H)_2$ with 2,4-bistrichloromethyl-6-(mono- or dihydroxyphenyl)-1,3,5-triazines. The esters have the formulae I or II:

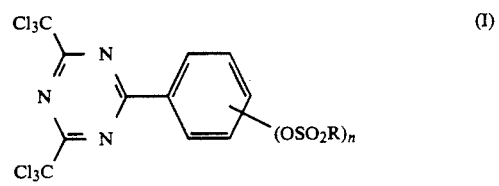

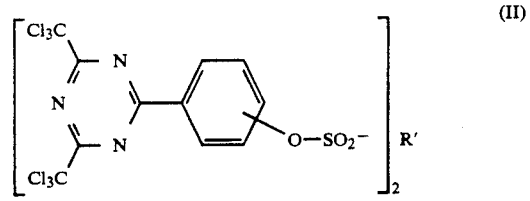

where R is an optionally further substituted $(C_1-C_{10})$-alkyl, $(C_5-C_{10})$cycloalkyl, $(C_6-C_{10})$aryl, $(C_6-C_{10})$aryl-$(C_1-C_{10})$alkyl or $(C_3-C_9)$heteroaryl radical, R' is an optionally substituted $(C_1-C_{10})$alkylene, $(C_6-C_{10})$arylene or $(C_3-C_9)$heteroarylene radical, and n may be 1 or 2. In the case where n=2 the radicals R may also be different. The radicals R and R' may be substituted with at least one substituent selected from the group comprising $(C_1-C_8)$ alkyl, $(C_1-C_8)$alkoxy, $(C_1-C_8)$ alkanoyl, $(C_1-C_8)$ alkanoyloxy, $(C_6-C_{10})$ aryl, cyano or halogen.

As the following examples show, the radicals R and R' may optionally also contain other substituents, e.g., methyl, ethyl, propyl, isopropyl, butyl, hexyl, octyl, decyl, dodecyl, hexadecyl, octadecyl, 10-camphyl, chloromethyl, 2-chloroethyl, 3-chloropropyl, dichloromethyl, trichloromethyl, difluoromethyl, trifluoromethyl, 2,2,2-trifluoroethyl, 1,1,2,3,3,3-hexafluoropropyl, perfluorohexyl, trimethylsilylmethyl, methanesulfonylmethyl, phenyl, benzyl, 4-acetylphenyl, 4-acetylaminophenyl, 2-, 3- or 4-bromophenyl, 2-, 3- or 4-chlorophenyl, 2-, 3- or 4-fluorophenyl, 4-iodophenyl, 2-, 3- or 4-methylphenyl, 4-ethylphenyl, 4-propylphenyl, 4-isopropylphenyl, 4-isobutylphenyl, 4-tert-butylphenyl, 4-tert-amylphenyl, 4-hexylphenyl, 4-methoxyphenyl, 4-butoxyphenyl, 4-hexadecyloxyphenyl, 2-, 3- or 4-trifluoromethylphenyl, 2- or 4-trifluoromethoxyphenyl, 2-, 3- or 4-nitrophenyl, 3- or 4-carboxyphenyl, 2-methoxycarbonylphenyl, 4-tetrafluoroethoxyphenyl, β-styryl, 4-acetylamino-3-chlorophenyl, 4-acetylamino-3-fluorophenyl, 3,5-bistrifluoromethylphenyl, 2,5-bis(2,2,2-trifluoroethoxy)phenyl, 2,5-dimethylphenyl, 2,4-, 2,5- or 3,4-dimethoxyphenyl, 2,4-diisopropylphenyl, 5-bromo-2-methoxyphenyl, 2- or 3-chloro-4-fluorophenyl, 3-chloro-2-methylphenyl, 3-chloro-4-methoxyphenyl, 2-chloro-6-methylphenyl, 2-chloro-4-trifluoromethylphenyl, 5-chloro-2-methoxyphenyl, 5-fluoro-2-methylphenyl, 2,5- or 3,4-dibromophenyl, 2,3-, 2,4- or 2,5-, 2,6-, 3,4- or 3,5-dichlorophenyl, 2-(2,4-dichlorophenoxy)phenyl, 4-(2-chloro-6-nitrophenoxy)-phenyl, 2,4- or 2,5-difluorophenyl, 3-carboxy-4-chlorophenyl, 4-chloro-3-nitrophenyl, 2-methyl-5-nitrophenyl, 4-chloro-3- or 2-chloro-5-trifluoromethylphenyl, 4- (2,2-dichlorocyclopropyl)phenyl, 2,4-dinitrophenyl, 4-dimethylamino-3-nitrophenyl, 2-nitro-4-trifluoromethylphenyl, 2,4,6-trimethylphenyl, 2,4,6-triisopropylphenyl, 2,3,4-, 2,4,5- or 2,4,6-trichlorophenyl, 4-chloro-2,5-dimethylphenyl, 2,4-dichloro-5-methylphenyl, 3,5-dichloro-2-hydroxyphenyl, 3,5-dichloro-4-(4-nitrophenoxy)phenyl, 4-(2-chloro-4-nitrophenoxy)-3,5-dichlorophenyl, 4-bromo-2,5-difluorophenyl, 2,4-dimethyl-3-nitrophenyl, 3,5-dinitro-4-methylphenyl, 2,3,5,6-tetramethylphenyl, 4-methoxy-2,3,6-trimethylphenyl, 2,5-dibromo-3,6-difluorophenyl, 2,3,4,5,6-pentafluorophenyl, 1- or 2-naphthyl, 5-diazo-6-oxo-5,6-dihydro-1-naphthyl, 6-diazo-5-oxo-5,6-dihydro-i-naphthyl, 5-diazo-6-oxo-5,6-dihydro-8-naphthyl,5-diazo-3-methoxy-6-oxo-5,6-dihydro-8-naphthyl, 5-dimethylamino-1-naphthyl, 1-anthracenyl, 2-anthraquinonyl, 8-quinolinyl, 2-thienyl, 5-chloro-2-thienyl, 4-bromo-2,5-dichloro-3-thienyl, 4,5-dibromo-2-thienyl, 2,3-dichloro-5-thienyl, 2-bromo-3-chloro-5-thienyl, 3-bromo-2-chloro-5-thienyl, 3-bromo-5-chloro-2-thienyl, 2,5-dichloro-3-thienyl, 2-(2-pyridyl)-5-thienyl, 5-chloro-1,3-dimethyl-4-pyrazolyl, 3,5-dimethyl-4-isoxazolyl, 2,4-dimethyl-5-thiazolyl, 2-acetylamino-4-methyl-5-thiazolyl, 1,4-butylene, 2-oxo-1, 3-propylene, 1,2- or 1,3-phenylene, 3-methyl-1,2-phenylene, 2,4,6-trimethyl-1,3-phenylene, 4,4'-biphenylene, 4,4'-methylenediphenylene, 4,4'-oxybiphenylene, 1,5-naphthylene, 2-chloro-3,5-thienylene, 2-(1-methyl-5-trifluoromethyl-3-pyrazolyl) -3,5-thienylene.

There are no restrictions with respect to the position of the hydroxyl group(s) on the aromatic benzene ring, i.e., the corresponding cyanophenol precursors can be freely chosen in relation to the substitution pattern. Of the compounds of the formula I, those with n=1 are preferred.

The radiation-sensitive mixture according to the invention contains
(a) a compound which forms strong acid on exposure to actinic radiation,
(b) a compound containing at least two acid-crosslinkable groups, and
(c) a water-insoluble polymer binder which is soluble or at least swellable in aqueous-alkaline solutions, and is one wherein the compound (a) is an ester of a sulfonic acid or sulfonic acids of the formula R—SO$_3$H or R'(—SO$_3$H)$_2$ with 2,4-bistrichloromethyl-6-(mono- or dihydroxyphenyl)-1,3,5-triazine having the above-mentioned chemical structure.

In special radiation-sensitive mixtures, incompletely esterified products, i.e., those which still contain free phenolic hydroxyl groups, may preferably be used to improve the solubility in common resist solvents and/or to optimize the solubility rate conditions.

The preparation of the esters,, in accordance with the invention, of sulfonic acids of the formula R—SO$_3$—H or R'(—SO$_3$H)$_2$ with 2,4-bistrichloromethyl-6-(mono- or dihydroxyphenyl)-1,3,5-triazines is known per se. The starting materials used in this process are primarily cyanophenols and the corresponding sulfonyl chlorides. Processes for preparing aromatic sulfonic acid esters are described, for example, by F. Muth in Houben-Weyl-Müller, METHODEN DER ORGANISCHEN CHEMIE (METHODS OF ORGANIC CHEMISTRY), vol. IX, page 633 (and the literature references cited there), THIEME-VERLAG, 4th edition, Stuttgart 1955, by S. Pawlenko, loc. cit., vol. E 11, page 1084, THIEME-VERLAG, 1st edition, Stuttgart 1985, and in the patent literature using numerous examples. The corresponding sulfonyl anhydrides are also suitable as starting materials (see S. Pawlenko, loc. cit., vol. E 11, page 1086, THIEME-VERLAG, 1st edition, Stuttgart 1985, and P. J. Stang, M. Hanack, L. R. Subramaniam, SYNTHESIS, 1982, 85). This applies in particular to the benzenesulfonyl anhydrides substituted with perfluoroalkyl groups. The preparation of the esters of sulfonic acids of the formula R—SO$_3$H or R'(—SO$_3$H)$_2$ with 2,4-bistrichloromethyl-6-(mono- or dihydroxyphenyl)-1,3,5-triazines from the esters of the corresponding cyanophenols with sulfonic acids R—SO$_3$H was carried out analogously to EP 137 452.

The radiation-sensitive mixture according to the invention is remarkable for its high sensitivity over a wide spectral range. During processing under practical conditions, no limitations were observed with respect to the solubility in common resist solvents and with respect to the evaporation of radiation-sensitive components (a) from the layer. The radiation-sensitive mixture has a high thermal stability and can reproduce in exact detail even the finest structures of an original.

Surprisingly, the quantum yield on irradiating the mixtures according to the invention is higher than the yield on irradiating known mixtures containing 2,4-bistrichloromethyl-1,3,5-triazines. This higher acid-formation efficiency indicates that not only hydrohalic acids, but also, to a lesser extent, sulfonic acids, are generated during irradiation and contribute to an increased sensitivity in the mixture according to the invention. The suitability of the acid formers according to the invention of the general formula I in negative-working mixtures was therefore not obvious since, inter alia, readily soluble cleavage products (phenols and sulfonic acids) are formed during irradiation in the regions to be cross-linked.

The negative-working radiation-sensitive mixtures according to the invention exhibit not only a high thermal resistance and plasma resistance, but also outstanding lithographic properties making resolution possible in the semimicrometer and in some cases even in the subsemimicrometer region. After the imagewise irradiation and subsequent development a mask image is obtained which is faithful to detail. The resist areas have steep edges. In the unirradiated regions, the resist layer is completely stripped, i.e., no remains or residues of the layer are left behind on the substrate. The acids formed during the photolysis result in an efficient crosslinking of the resist components (b) and (c) and this makes it possible to produce highly sensitive negative-working mixtures.

In the radiation-sensitive mixture according to the invention, the ester of a sulfonic acid or sulfonic acids of the formula $R-SO_3H$ or $R'(-SO_3H)_2$ with 2,4-bistrichloromethyl-6-(mono- or dihydroxyphenyl)-1,3,5-triazine forms an acid on irradiation. It may be used alone or in combination with other acid formers such as halogen compounds, particularly trichloromethyltriazine derivatives or trichloromethyloxadiazole derivatives, onium salts, 1,2-disulfones, o-(quinonediazide)sulfonyl chlorides or organometal/organohalogen combinations. Mixtures with bis(sulfonyl)diazomethanes and sulfonylcarbonyldiazomethanes are also suitable. In such mixtures, however, the disadvantages mentioned at the outset may occur again.

Recording materials produced with the mixtures according to the invention exhibit, surprisingly, an image differentiation which satisfies the highest requirements and, still more surprisingly, an improvement in the contrast and the resolving power. The mixtures according to the invention make it possible, for example, to produce a highly sensitive negative-working photoresist for high-energy UV2 radiation, for example, at 248 nm.

Since the mixture according to the invention is sensitive over a wide spectral range, actinic radiation is generally suitable for the imagewise irradiation. In this context, actinic radiation is to be understood as meaning any radiation whose energy corresponds at least to that of short-wave visible light. In this context, UV radiation in the range from 190 to 450 nm, preferably from 200 to 400 nm, particularly preferably from 200 to 300 nm, and also electron radiation or X-rays are suitable.

The proportion of esters of the formula $R-SO_3H$ or $R'(-SO_3H)_2$ with 2,4-bistrichloromethyl-6-(mono- or dihydroxyphenyl)-1,3,5-triazines in the mixture according to the invention is generally about 0.25 to 15% by weight, preferably about 0.5 to 5% by weight, based on the total weight of solids in the mixture.

Particularly suitable acid-crosslinkable compounds (b) are the resols disclosed in GB 2,082,339. In addition, aromatics substituted with alkoxymethyl or oxiranylmethyl groups (EP 212 482), and monomeric and oligomeric melamine/formaldehyde or urea/formaldehyde condensates (EP 133 216, DE 36 34 371, DE 37 11 264) may be used. Examples of the first type are, in particular, the commercially obtainable resol products ®Bakelite R 5363, ®Bakelite R 17620, ®Bakelite R 10282 and ®Kelrez 40-152. However, resol derivatives are on the whole not preferred since they have comparatively high absorptions in the deep ultraviolet range and consequently result in an impairment of the image reproduction.

Better suited are the crosslinking agents of the general formula III disclosed by EP 212 482:

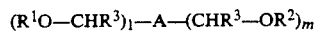

(III)

in which

A is —B— or —B—Y—B— and

B is an optionally substituted mononuclear aromatic hydrocarbon or an oxygen- or sulfur-containing heterocyclic aromatic compound, Y is a single bond, $(C_1-C_4)$alkylene or $(C_1-C_4)$alkylenedioxy radical whose chains may be interrupted by oxygen atoms, —O—, —S—, —SO$_2$—, —CO—, —CO$_2$—, —O—CO$_2$—, —CONH— or —O—C$_6$H$_4$O—, $R^1$ and $R^2$ are hydrogen, $(_1-C_6)$alkyl, $C_5$ or $C_6$-cycloalkyl, optionally substituted $(C_6-C_{12})$aryl, $(C_6-C_{12})$aralkyl or acyl, $R^3$ is hydrogen, $(C_1-C_4)$alkyl or optionally substituted phenyl, l is an integer from 1 to 3, and m is an integer from 0 to 3, l+m being at least 2.

Typical crosslinking agents are aromatics and heterocyclics which are polysubstituted with hydroxymethyl, acetoxymethyl and methoxymethyl groups. Other preferred crosslinking agents are melamine/formaldehyde derivatives that contain, for example, at least two free N-hydroxymethyl, N-alkoxymethyl or N-acyloxymethyl groups. In particular, the N-alkoxymethyl derivatives are suitable for use in the radiation-sensitive mixture according to the invention. The crosslinking agents are capable of crosslinking with the polymeric binders at elevated temperatures under the influence of the photolytically-produced acids. Generally, they are agents that are capable of forming a carbonium ion under the temperature and acid conditions mentioned.

The proportion of the acid-crosslinkable compound (b) in the radiation-sensitive mixture according to the invention is expediently about 1 to 50% by weight, preferably about 5 to 25% by weight, based in all cases on the total weight of the solid constituents of the mixture.

The radiation-sensitive mixture according to the invention contains at least one polymeric water-insoluble binder (c) that is soluble, or at least swellable, in aqueous-alkaline solutions. The binder is particularly distinguished by the fact that it has good compatibility with the other constituents of the radiation-sensitive -mixture according to the invention and has a self-absorption that is as low as possible, i.e., a high transparency, particularly in the wavelength range from 190 to 300 nm. Binders based on novolak condensation resins that are generally used in combination with naphthoquinone diazides as photoactive components do not fulfill this condition. Although novolak condensation resins exhibit a reduction in the solubility in relation to aqueous-alkaline developers in the unexposed regions after imagewise exposure, their self-absorption in the short-wavelength region desired for the irradiation is undesirably high.

Novolak condensation resins may, however, be used in a mixture with other resins which are suitable as binders and have relatively high transparency. In this connection, the mixing ratios depend predominantly on the nature of the binder to be mixed with the novolak. In particular, its degree of self-absorption in the wavelength range mentioned and also its miscibility with the other constituents of the radiation-sensitive mixture play a decisive role. Generally, however, the binder of the radiation-sensitive mixture according to the invention may contain up to about 30% by weight, in particular up to about 20% by weight, of a novolak condensation resin. The binder (mixture) advantageously has an absorbance of less than about 0.5 $\mu m^{-1}$, preferably less than about 0.3 $\mu m^{-1}$, for radiation of the wavelength 248 nm.

Suitable binders include homopolymers or copolymers of p-hydroxystyrene and its alkyl derivatives, for example, of 3-methyl-4-hydroxystyrene, homopolymers or copolymers of other vinylphenols, for example, of 3-hydroxystyrene, and of the esters or amides of acrylic acid with aromatics containing phenolic groups. The comonomers used may be polymerizable compounds such as styrene, methyl (meth)acrylate or the like.

Mixtures with increased plasma resistance are obtained if silicon-containing vinyl monomers, for example, vinyltrimethylsilane, are concomitantly used to prepare the binders. The transparency of said binders is generally higher in the region of interest, with the result that improved structuring is possible.

Homopolymers or copolymers of maleimide may be used with equal success. These binders also exhibit high transparency in the wavelength range described. Here again the comonomers used are preferably styrene, substituted styrenes, vinyl ethers, vinyl esters, vinylsilyl compounds or (meth)acrylates. Copolymers of styrene with comonomers which increase solubility in aqueous-alkaline solutions may also be used. These include, for example, maleic anhydride and half-esters of maleic acid.

The binders may be mixed, provided the optical quality of the radiation-sensitive mixture is not thereby impaired. Binder mixtures are, however, not preferred. The glass transition temperature of the binder or the binder mixture is advantageously at least about 120° C. The proportion of binder is generally about 40 to 95% by weight, in particular about 50 to 90% by weight, based on the total weight of the solid components of the radiation-sensitive mixture.

Optionally, dyes, pigments, plasticizers, wetting agents and levellers, and also polyglycols, cellulose ethers, for example, ethylcellulose, may be added to the radiation-sensitive mixtures according to the invention to fulfill special requirements, such as flexibility, adhesion and gloss.

If a substrate is to be coated, the radiation-sensitive mixture according to the invention is expediently dissolved in a solvent or in a combination of solvents. Ultimately, the choice of solvent or solvent mixture depends on the coating process applied, the desired layer thickness and the drying conditions. The solvent must also be chemically inert to the other layer constituents under the application conditions. Particularly suitable solvents and the coating processes applied are comprehensively described in German Patent Application P 41 12 971.7 and apply here analogously. The solution prepared with the solvents mentioned generally has a solids content of about 5 to 60% by weight, preferably up to about 50% by weight.

Finally, the invention also relates to a radiation-sensitive recording material consisting essentially of a substrate and a radiation-sensitive layer situated thereon that comprises a radiation-sensitive mixture according to the invention.

Suitable substrates are all the materials of which capacitors, semiconductors, multilayer printed circuits or integrated circuits are composed or from which they can be prepared. An adhesion promoter is optionally used. The substrates, adhesion promoters and base materials disclosed by German Patent Application P 41 12 971.7 for producing photomechanical recording layers are also applied here analogously.

The recording material according to the invention is imagewise exposed to actinic radiation. Suitable radiation sources are also comprehensively described in the above-mentioned publication and are used here accordingly.

The thickness of the photosensitive layer depends on the application purpose. Generally, it is between about 0.1 and 100 $\mu$m, preferably between about 0.5 and 10 $\mu$m, particularly preferably around 1.0 $\mu$m.

The invention also relates to a process for producing a radiation-sensitive recording material. P 41 12 971.7 describes application of the radiation-sensitive mixture to the substrate, the aqueous solutions suitable as developer, the postcuring of the developed layer structures and the use of the radiation-sensitive mixture according to the invention in the production of integrated circuits or of individual electrical modules using lithographic processes.

The radiation-sensitive mixtures according to the invention have a high photosensitivity, particularly when irradiated with light having a wavelength between 190 and 300 nm. Since the mixtures have a markedly high transparency in the desired wavelength range, finer structures can be obtained than is possible with known mixtures. The developed resist layer is used under these circumstances as a mask for the subsequent processing steps. Such steps are, for example, the etching of the layer base, the implantation of ions in the layer base or the deposition of metals or other materials on the layer base.

The examples described below illustrate the invention but are not intended to make any restriction. In the following, pbw stands for parts by weight and pbv for parts by volume. The relationship between pbw and pbv is the same as that between g and cm$^3$.

PREPARATION EXAMPLE 1

Stage 1: 4-Cyanophenol (25.0 pbw) and 31.2 pbw of triethylamine are dissolved in 200 pbw of tetrahydrofuran and cooled to 50° C. While stirring and keeping the temperature constant, 39.8 pbw of p-toluenesulfonyl chloride dissolved in 50 pbw of tetrahydrofuran are added dropwise. The mixture is brought to room temperature, stirred for an additional 2 hours, then stirred into 1,000 pbv of distilled water. After acidification to a pH of 2 to 3, the precipitate is filtered off by suction, washed with water until neutral and then dried. The crystalline material is recrystallized from isopropanol. An amount of 53 pbw of 4-(toluene-4-sulfonyloxy)benzonitrile (white crystals having a melting point of 85° C.) is obtained.

Stage 2: An amount of 13. 6 pbw of the compound described above is dissolved in 43.4 pbw of trichloroacetonitrile with moisture excluded and 2.7 pbw of aluminum bromide are added. Dry hydrogen chloride gas is passed into this mixture at 24° to 30° C. until saturation is reached. The solidifying mixture is allowed to stand for 24 hours at room temperature. It is then taken up in 400 pbw of methylene chloride and washed twice, using 100 pbw of water each time. The organic phase is dried, filtered and evaporated. The residue is recrystallized from ethanol. An amount of 23.5 pbw of 2,4-bistrichloromethyl-6-[4-(toluene-4-sulfonyloxy)-phenyl]-1,3,5-triazine (white crystals having a melting point of 156° C.) is obtained.

PREPARATION EXAMPLE 2

Stage 1: 4-Cyanophenol (25.0 pbw) and 31.2 pbw of triethylamine are dissolved in 200 pbw of tetrahydrofuran and cooled to 5° C. While stirring and keeping the temperature constant, 23.3 pbw of methanesulfonyl chloride dissolved in 50 pbw of tetrahydrofuran are added dropwise. The mixture is brought to room temperature, stirred for an additional 2 hours, then stirred into 1,000 pbv of distilled water. After acidification to a pH of 2 to 3, the precipitate is filtered off by suction, washed with water until neutral and dried. The crystalline material is recrystallized from isopropanol. An amount of 35 pbw of 4-methanesulfonyloxybenzonitrile (white crystals having a melting point of 93° C.) is obtained.

Stage 2: An amount of 9.8 pbw of the compound described above is dissolved in 43.4 pbw of trichloroacetonitrile with moisture excluded and 2.7 pbw of aluminum bromide are added. Dry hydrogen chloride gas is passed into this mixture at 24° to 30° C. until saturation is reached. The solidifying mixture is allowed to stand for 24 hours at room temperature. It is taken up in 400 pbw of methylene chloride and washed twice, using 100 pbw of water each time. The organic phase is dried, filtered and evaporated. The residue is recrystallized from ethanol. An amount of 13.8 pbw of 2,4-bistrichloromethyl-6- (4-methanesulfonyloxyphenyl)-1,3,5-triazine (white crystals having a melting point of 142° C.) is obtained.

PREPARATION EXAMPLE 3

Stage 1: 4-Cyanophenol (11.9 pbw) and 15.0 pbw of triethylamine are dissolved in 120 pbw of tetrahydrofuran and cooled to 0° C. While stirring and keeping the temperature constant, 22.6 pbw of naphthalene-2-sulfonyl chloride dissolved in 50 pbw of tetrahydrofuran are added dropwise to this mixture. The mixture is brought to room temperature, stirred for an additional 2 hours, then stirred into 1,000 pbv of distilled water. After acidification to a pH of 2 to 3, the precipitate is filtered off by suction, washed with water until neutral and dried. The crystalline material is recrystallized from isopropanol. An amount of 25.3 pbw of 4-(naphthalene-2-sulfonyloxy)benzonitrile (white crystals having a melting point of 112° C.) is obtained.

Stage 2: An amount of .23.2 pbw of the compound described above is dissolved in 65.0 pbw of trichloroacetonitrile with moisture excluded and 4.0 pbw of aluminum bromide are added. Dry hydrogen chloride gas is passed into this mixture at 24° to 30° C. until saturation is reached. The solidifying mixture is allowed to stand for 24 hours at room temperature. It is then taken up in 400 pbw of methylene chloride and washed twice, using 100 pbw of water each time. The organic phase is dried, filtered and evaporated. The residue is recrystallized from ethyl acetate. An amount of 32.5 pbw of 2,4-bistrichloromethyl-6-[4-(naphthalene-2-sulfonyloxy)phenyl]-1,3,5-triazine (white crystals having a melting point of 175° C.) is obtained.

PREPARATION EXAMPLE 4

Stage 1: 4-Cyanophenol (6.0 pbw) and 7.5 pbw of triethylamine are dissolved in 200 pbw of tetrahydrofuran and cooled to 5° C. While stirring and keeping the temperature constant, 10.3 pbw of 4-methoxybenzenesulfonyl chloride dissolved in 50 pbw of tetrahydrofuran are added dropwise to this mixture. The mixture is brought to room temperature, stirred for an additional 2 hours, then stirred into 1,000 pbv of distilled water. After acidification to a pH of 2 to 3, the precipitate is filtered off by suction, washed with water until neutral and dried. The crystalline material is recrystallized from isopropanol. An amount of 13 pbw of 4-(4-methoxybenzenesulfonyloxy)benzonitrile (white crystals having a melting point of 128° C.) is obtained.

Stage 2: An amount of 11. 6 pbw of the compound described above is dissolved in 35.0 pbw of trichloroacetonitrile with moisture excluded and 2.5 pbw of aluminum bromide are added. Dry hydrogen chloride gas is passed into this mixture at 24° to 30° C. until saturation is reached. The solidifying mixture is allowed to stand for 24 hours at room temperature. It is taken up in 300 pbw of methylene chloride and washed twice, using 100 pbw of water each time. The organic phase is dried, filtered and evaporated. The residue is recrystallized from ethyl acetate. An amount of 16.8 pbw of 2,4-bistrichloromethyl-6-[4-(4-methoxybenzenesulfonyloxy)phenyl]-1,3,5-triazine (white crystals having a melting point of 168° C.) is obtained.

PREPARATION EXAMPLE 5

Stage 1: 3-Cyanophenol (4.0 pbw) and 5.1 pbw of triethylamine are dissolved in 100 pbw of tetrahydrofuran and cooled to 5° C. While stirring and keeping the temperature constant, 10.0 pbw of 2,4,6-triisopropylbenzenesulfonyl chloride dissolved in 50 pbw of tetrahydrofuran are added dropwise to this mixture. The mixture is brought to room temperature, stirred for an additional 2 hours, then stirred into 1,000 pbv of distilled water. After acidification to a pH of 2 to 3, the precipitate is filtered off by suction, washed with water until neutral and dried. The crystalline material is recrystallized from isopropanol. An amount of 12 pbw of 3-(2,4,6-triisopropylbenzenesulfonyloxy)benzonitrile (white crystals having a melting point of 70° C.) is obtained.

Stage 2: An amount of 11. 5 pbw of the compound described above is dissolved in 26.0 pbw of trichloroacetonitrile with moisture excluded and 2. 0 pbw of aluminum bromide are added. Dry hydrogen chloride gas is passed into this mixture at 24° to 30° C. until saturation is reached. The solidifying mixture is allowed to stand for 24 hours at room temperature. It is taken up in 200 pbw of methylene chloride and washed twice, using 100 pbw of water each time. The organic phase is dried, filtered and evaporated. The residue is recrystallized from ethyl acetate. An amount of 10.5 pbw of 2,4-bistrichloromethyl-6-[3-(2,4,6-triisopropylbenzenesulfonyloxy)phenyl]-1,3,5-triazine (white crystals having a melting point of 156° C.) is obtained.

PREPARATION EXAMPLE 6

Stage 1: 2-Cyanophenol (11.9 pbw) and 15.2 pbw of triethylamine are dissolved in 100 pbw of tetrahydrofuran and cooled to 5° C. While stirring and keeping the temperature constant, 11.4 pbw of methanesulfonyl chloride dissolved in 50 pbw of tetrahydrofuran are added dropwise to this mixture. The mixture is brought to room temperature, stirred for an additional 2 hours, then stirred into 1,000 pbv of distilled water. After acidification to a pH of 2 to 3, the precipitate is filtered off by suction, washed with water until neutral and dried. The crystalline material is recrystallized from isopropanol. An amount of 13.5 pbw of 2-methanesulfonyloxybenzonitrile (white crystals having a melting point of 58° C.) is obtained.

Stage 2: An amount of 12. 8 pbw of the compound described above is dissolved in 56.6 pbw of trichloroacetonitrile with moisture excluded and 2. 0 pbw of aluminum bromide are added. Dry hydrogen chloride gas is passed into this mixture at 24° to 30° C. until saturation is reached. The solidifying mixture is allowed to stand for 24 hours at room temperature. It is taken up in 200 pbw of methylene chloride and washed twice, using 100 pbw of water each time. The organic phase is dried, filtered and evaporated. The residue is recrystallized from isopropanol. An amount of 15.7 pbw of 2,4-bistrichloromethyl-6-(2-methanesulfonyloxyphenyl-1,3,5-triazine (white crystals having a melting point of 86° C.) is obtained.

PREPARATION EXAMPLES 7 TO 13

Further compounds of the formula I are disclosed which were prepared analogously to the examples described hitherto. Selected representatives of the possible variations described in the formula I are characterized in the table below. As an analytical value, the quantitative determination of the sulfur and the chlorine content is sufficiently informative.

| No. | Position* | R | M.p. [°C.] | Elemental analysis | | | |
|---|---|---|---|---|---|---|---|
| | | | | % Cl | | % S | |
| | | | | calc. | found | calc. | found |
| 7 | para | $-C_6H_5$ | 140 | 38.8 | 38.2 | 5.8 | 5.3 |
| 8 | para | $-2,4,5-(Cl)_3-C_6H_2$ | 190 | 49.0 | 49.0 | 4.9 | 5.2 |
| 9 | para | $4-Cl-C_6H_4$ | 150 | 42.6 | 43.1 | 5.5 | 5.4 |
| 10 | para | $4-Br-C_6H_4$ | 148 | 33.9 | 34.2 | 5.1 | 5.2 |
| 11 | meta | $4-CH_3-C_6H_4$ | 162 | 37.8 | 38.1 | 5.7 | 6.0 |
| 12 | meta | $-CH_3$ | 120 | 43.8 | 48.5 | 6.6 | 5.9 |
| 13 | ortho | $4-CH_3-C_6H_4$ | 86 | 37.8 | 39.4 | 5.7 | 6.1 |

*Based on the position of the 2,4-bistrichloromethane-1,3,5-triazin-6-yl group on the benzene ring.

Others of the esters described above of sulfonic acids of the formula $R-SO_3H$ or $R'(-SO_3H)_2$ with 2,4-bistrichloromethyl-6-(mono- or dihydroxyphenyl) -1,3,5-triazines can also be prepared analogously.

The esters of sulfonic acid or sulfonic acids of the formula $R-SO_3H$ or $R'(-SO_3H)_2$ with 2,4-bistrichloromethyl-6-(mono- or dihydroxyphenyl)-1,3,5-triazines were characterized by $^1H$ high-field nuclear resonance spectra, by elemental analyses and by IR spectroscopy to demonstrate the absence of free hydroxyl groups in the product.

APPLICATION EXAMPLES

Examples 1 to 7 confirm the suitability of the mixture according to the invention for recording materials in microlithography. The superiority of the mixtures according to the invention is confirmed on the basis of Comparison Examples 8 and 9. Examples 10 and 11 document the applicability of the mixture in printed circuits and lithographic plates.

The coating solutions were filtered through a filter having a pore diameter of 0.2 μm and spun onto a wafer pretreated with an adhesion promoter (hexamethyldisilazane). In this process the spin speed was chosen such that layer thicknesses of around 1.05 μm were obtained after drying for 1 minute at 100° C. on the hot plate.

Unless otherwise stated in the individual examples, the recording material was imagewise exposed under an original using the radiation of a KrF excimer laser (248 nm) or a xenon/mercury-vapor lamp (260 nm, with interference filter) and then subjected to a post-exposure bake on a hot plate for 1 minute at 100° C.

The recording material was developed with a 0.27N aqueous tetramethylammonium hydroxide solution.

EXAMPLE 1

A photosensitive recording material was produced with the aid of a coating solution composed of
- 7.5 pbw of a copolymer of styrene and maleimide (molar ratio 50:50) having a softening range of 165° to 180° C.,
- 2.0 pbw of hexa-N-acetoxymethylmelamine, and
- 0.075 pbw of 2,4-bistrichloromethyl-6-[4-(4-methoxyphenylsulfonyloxy)phenyl]-1,3,5-triazine in accordance with Preparation Example 4, in
- 42 pbw of propylene glycol monomethyl ether acetate.

Softbake: 1 min, 110° C., hot plate
Exposure: 3.8 mJ/cm$^2$ (xenon/mercury-vapor lamp)
Post-exposure bake: 2 min, 120° C., hot plate
Development: 120 s (0.02N aqueous tetramethylammonium hydroxide solution)

EXAMPLE 2

A photosensitive recording material was produced with the aid of a coating solution composed of
- 7.5 pbw of the copolymer specified in Example 1,
- 2.5 pbw of 4,4'-bis (methoxymethyl)diphenylether, and
- 0.15 pbw of 2,4-bistrichloromethyl-6-[3-(toluene-4-sulfonyloxy)phenyl]-1,3,5-triazine in accordance with Preparation Example 11, in
- 42 pbw of propylene glycol monomethyl ether acetate.

Softbake: 1 min, 110° C., hot plate
Exposure: 2.8 mJ/cm$^2$ (xenon/mercury-vapor lamp)
Post-exposure bake: 2 min, 115° C., hot plate
Development: 90 s (0.02N aqueous tetramethylammonium hydroxide solution)

EXAMPLE 3

A photosensitive recording material was produced with the aid of a coating solution composed of
- 7.5 pbw of a homopolymer of 3-methyl-4-hydroxystyrene having a softening range of $\geq 150°$ C. (GPC),
- 2.5 pbw of a cresol/formaldehyde resol, and
- 0.14 pbw of 2,4-bistrichloromethyl-6-[4-(toluene-4-sulfonyloxy)phenyl]-1,3,5-triazine in accordance with Preparation Example 1, in
- 42 pbw of propylene glycol monomethyl ether acetate.

Exposure: 2.9 mJ/cm$^2$ (xenon/mercury-vapor lamp)
Development: 90 s

EXAMPLE 4

A photosensitive recording material was produced with the aid of a coating solution in accordance with Example 3, with the difference that, instead of 2.5 pbw of a cresol/formaldehyde resol (®Bakelite R5363), 2.0 Pbw of hexa-N-methoxymethylmelamine were used.
Exposure: 2.7 mJ/cm$^2$ (KrF excimer laser)
Development: 105 s

EXAMPLE 5

A photosensitive recording material was produced with the aid of a coating solution composed of 7.5 pbw of a copolymer of styrene/4-hydroxystyrene (molar ratio 20:80) having an average molecular weight of around 30,000 (GPC),
2.5 pbw of hexa-N-butoxymethylmelamine, and
0.1 pbw of 2,4-bistrichloromethyl-6-[4-(2,4,5-trichlorobenzenesulfonyloxy)phenyl]-1,3,5-triazine in accordance with Preparation Example 8, in
42 pbw of propylene glycol monomethyl ether acetate.
Softbake: 1 min, 90° C., hot plate
Exposure: 3.4 mJ/cm$^2$ (KrF excimer laser)
Post-exposure bake: 120 s, 100° C., hot plate
Development: 120 s (0.135N aqueous tetramethylammonium hydroxide solution)

EXAMPLE 6

A photosensitive recording material was produced with the aid of a coating solution composed of 8.0 pbw of a copolymer of 3-methyl-4-hydroxystyrene/p-hydroxystyrene (molar ratio 75:25) having a softening range of >150° C. and an average molecular weight of 28,000 (GPC),
2.0 pbw of hexa-N-methoxymethylmelamine, and
0.05 pbw of 2,4-bistrichloromethyl-6-(4-benzenesulfonyloxyphenyl)-1,3,5-triazine in accordance with Preparation Example 7, in
42 pbw of propylene glycol monomethyl ether acetate.
Exposure: 4.1 mJ/cm$^2$ (xenon/mercury-vapor lamp)
Development: 75 s

EXAMPLE 7

A photosensitive recording material was produced with the aid of a coating solution composed of 7.5 pbw of the copolymer specified in Example 1,
2.5 pbw of 4,4'-bis(methoxymethyl)diphenylsulfone, and
0.1 pbw of 2,4-bistrichloromethyl-6-(4-methanesulfonyloxyphenyl)-1,3,5-triazine in accordance with Preparation Example 2, in
42 pbw of propylene glycol monomethyl ether acetate.
Exposure: 3.0 mJ/cm$^2$ (xenon/mercury vapor lamp)
Development: 75 s (0.02N aqueous tetramethylammonium hydroxide solution)

EVALUATION OF THE DEVELOPED RECORDING MATERIALS

The resist structures obtained in accordance with Examples 1 to 7 yielded a perfect negative image of the mask with steep resist edges, even structures in the subsemimicrometer region being reproduced in a true-to-detail manner. A scanning electron microscope examination revealed that the resist edges were aligned perpendicularly to the substrate surface.

The layer removal rates in the exposed resist regions were in all cases 15 nm/min and below.

EXAMPLES 8 AND 9 (COMPARISON EXAMPLES)

The resist formulation of Example 3 was modified by replacing the acid-forming compound used therein by the same quantity of 2,4-bistrichloromethyl-6-(4-methoxy-1-naphthalenyl)-1,3,5-triazine (photoinitiator No. 3 in Table 2 of DE 27 18 259) or 4,6,4',6'-tetrakistrichloromethyl-2,2'-p-phenylenebis-1-1,3,5-triazine prepared in accordance with the process specified in the reference.

The attempt to prepare a coating solution corresponding to the composition specified in Example 7 was unsuccessful since the acid-forming compound did not have an adequate solubility in the resist solvent in the concentration specified in Example 7. Only a markedly reduced concentration of the photoactive acid former resulted in a homogeneous coating solution. These resist formulations exhibited, however, a substantially reduced sensitivity (>8 mJ/cm$^2$) compared with the mixtures according to the invention.

Various experiments on irradiating a coated wafer (coated with a coating solution as described in Example 8) revealed marked differences in the photosensitivities. Analytical examinations of the coating solution using HPLC (high-pressure liquid chromatography) before and after the drying process (soft bake), without subsequent exposure step, revealed that appreciable quantities of the acid-forming compound evaporated from the layer. Although the order of magnitude of the sensitivity variations was less strongly pronounced than in comparable positive systems (see the simultaneously filed German Patent Application P 41 20 173.6), this behavior makes the control of the photosensitivity necessary for a practical process virtually impossible. In comparable investigations of the radiation-sensitive mixtures according to the invention, such a behavior was not observed in any case.

EXAMPLES 10

To produce an offset printing plate, a mechanically roughened and pretreated aluminum f oil was spin-coated with a coating solution of the following composition:

7.5 pbw of a cresol/formaldehyde novolak having a softening range of 105° to 120° C.,
2.5 pbw of a cresol/formaldehyde resol (®Bakelite R 5363),
0.2 pbw of 2,4-bistrichloromethyl-6-[4-(toluene-4-sulfonyloxy)phenyl]-1,3,5-triazine in accordance with Preparation Example 1, and
0.05 pbw of crystal violet base, in
90 pbw of propylene glycol monomethyl ether acetate.

After the layer had been dried (layer weight approximately 2.5 g/m$^2$), exposure was carried out for 45 seconds under a negative test original and the plate was heated after being stored for 10 minutes in a circulating air oven for 2 minutes at a temperature of 140° C. Development was carried out with a developer of the following composition:

0.5 pbw of sodium hydroxide,
0.8 pbw of sodium metasilicate nonahydrate, and
1.0 pbw of 2-n-butoxyethanol, in
97.7 pbw of fully demineralized water.

On development, a negative image of the original which was faithful to detail became visible. After rinsing with water, the plate was made ready for printing by wiping over with 1%-strength phosphoric acid. A total of 135,000 perfect impressions was obtained from this printing plate.

EXAMPLE 11

To produce an etching and galvanonegative dry resist, a solution of the following composition was prepared:

12.5 pbw of the novolak described in Example 10,
10.0 pbw of hexa-N-methoxymethylmelamine,
0.12 pbw of 2,4-bistrichloromethyl-6-[3-(2,4,6-triisopropylbenzenesulfonyloxy)phenyl]-1,3,5-triazine in accordance with Preparation Example 5, and
0.1 pbw of crystal violet, in
30 pbw of butanone.

A poly(ethylene terephthalate) film 25 μm thick which is standard for this purpose was coated with this solution so that a dry layer thickness of 18 μm resulted. The surface of the dry resist film was clad with a further poly (ethylene terephthalate) film. After peeling off the covering film, the dry film was laminated onto a glass sheet under pressure and heat. After cooling and peeling off the carrier film, the metal sheet was exposed through an original, in which process a good image contrast became visible. The material was stored for 10 minutes and then heated for 4 min at 95° C. The unexposed areas were spray developed with a developer of the composition specified in Example 10. The metal sheet was then etched through with commercial iron-(III) chloride solution down to the smooth edges. It is possible to process the shaped parts obtained still further before separation.

what is claimed is:

1. A negative-working radiation-sensitive mixture comprising
   (a) a compound which forms strong acid on exposure to actinic radiation,
   (b) a compound containing at least two acid-crosslinkable groups, and
   (c) a water-insoluble polymeric binder which is soluble or at least swellable in aqueous alkaline solutions, in an amount sufficient to produce a uniform film when a layer of the mixture is coated on a base, wherein the compound (a) is a radiation-sensitive ester of a sulfonic acid of the formula R—SO$_3$H or R'(—SO$_3$H)$_2$ with 2,4-bistrichloromethyl-6-(mono- or dihydroxyphenyl)-1,3,5-triazines, said ester being represented by one of formulae I and II

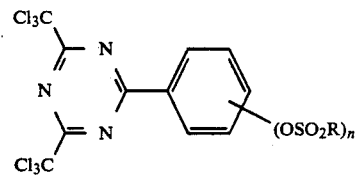

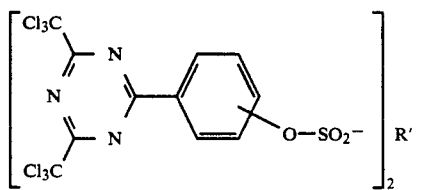

where R is an optionally further substituted (C$_1$-C$_{10}$alkyl, (C$_5$-C$_{10}$)cycloalkyl, (C$_6$-C$_{10}$)aryl, (C$_6$-C$_{10}$)aryl-(C$_1$-C$_{10}$)alkyl or (C$_3$-C$_9$)heteroaryl radical, R' is an optionally substituted (C$_1$-C$_{10}$)alkylene, (C$_6$-C$_{10}$)arylene or (C$_3$-C$_9$)heteroarylene radical, and n may be 1 or 2, and wherein compounds (a) and (b) are present in amounts sufficient to produce insoluble, crosslinked regions when a layer of the mixture is exposed to actinic radiation.

2. A negative-working radiation-sensitive mixture as claimed in claim 1, wherein the proportion of the compound (a) is about 0.25 to 15% by weight of the total weight of solids in the mixture.

3. A negative-working radiation-sensitive mixture as claimed in claim 1, wherein the compound (b) is a resol.

4. A negative-working radiation-sensitive mixture as claimed in claim 1, wherein the compound (b) is an aromatic compound substituted with a member selected from the group consisting of alkoxymethyl and oxiranylmethyl.

5. A negative-working radiation-sensitive mixture as claimed in claim 1, wherein the compound (b) is selected from the group consisting of melamine/formaldehyde condensate and a urea/formaldehyde condensate.

6. A negative-working radiation-sensitive mixture as claimed in claim 1, wherein the proportion of the compound containing at least two acid-crosslinkable groups (b) is about 1 to 50% by weight of the total weight of solids in the radiation-sensitive layer.

7. A negative-working radiation-sensitive mixture as claimed in claim 1, wherein the binder (c) contains phenolic hydroxyl groups.

8. A negative-working radiation-sensitive mixture as claimed in claim 1, wherein the binder (c) has an absorbance of less than 0.5 μm$^{-1}$ for radiation of the wavelength of 248 nm.

9. A negative-working radiation-sensitive mixture as claimed in claim 1, wherein the proportion of the binder (c) is from about 40 to 95% by weight of the total weight of solids in the mixture.

10. A negative-working radiation-sensitive recording material essentially comprising a base and a radiation-sensitive layer, wherein the layer contains a radiation-curable mixture as claimed in claim 1.

11. A negative-working radiation-sensitive mixture as claimed in claim 1, wherein the proportion of the compound (a) is about 0.5 to 5% by weight of the total weight of solids in the mixture.

12. A negative-working radiation-sensitive mixture as claimed in claim 1, wherein the proportion of the compound containing at least two acid-crosslinkable groups (b) is about 5 to 25% by weight of the total weight of solids in the radiation-sensitive layer.

13. A negative-working radiation-sensitive mixture as claimed in claim 1, wherein the binder (c) has an lot absorbance of less than 0.3 μm$^{-1}$ for radiation of the wavelength of 248 nm.

14. A negative-working radiation-sensitive mixture as claimed in claim 1, wherein the proportion of the binder (c) is from about 50 to 90% by weight of the total weight of solids in the mixture.

15. A negative-working radiation-sensitive mixture as claimed in claim 1, wherein the ester is 2,4-bistrichloromethyl-6-[4-(toluene-4-sulfonyloxy)phenyl]-1,3,5-triazine.

* * * * *